United States Patent [19]

Wagener

[11] 4,350,806

[45] Sep. 21, 1982

[54] BIOCOMPATIBLE COPOLYMERS

[75] Inventor: Kenneth B. Wagener, Asheville, N.C.

[73] Assignee: Akzona Incorporated, Asheville, N.C.

[21] Appl. No.: 306,110

[22] Filed: Sep. 28, 1981

[51] Int. Cl.$^3$ .................. C08G 63/44; C08G 69/44; C08G 73/16

[52] U.S. Cl. .................. 528/289; 525/437; 528/301

[58] Field of Search .............. 528/289, 301; 525/437

[56] References Cited

U.S. PATENT DOCUMENTS

| | | | |
|---|---|---|---|
| 3,562,352 | 2/1971 | Nyilas | 260/824 |
| 3,701,433 | 10/1972 | Krakaner et al. | 210/436 |
| 3,765,536 | 10/1973 | Rosenberg | 210/446 |
| 3,908,201 | 9/1975 | Jones et al. | 3/1 |
| 4,042,978 | 8/1977 | Jones et al. | 3/1 |
| 4,069,151 | 1/1978 | Higley et al. | 128/214 R |
| 4,075,108 | 2/1978 | Higley et al. | 210/500 M |
| 4,095,600 | 6/1978 | Casey et al. | 525/437 X |
| 4,101,422 | 7/1978 | Lamont et al. | 210/84 |
| 4,102,827 | 7/1978 | Rembaum et al. | 260/823 |
| 4,118,470 | 10/1978 | Casey et al. | 528/301 X |
| 4,122,072 | 10/1978 | Lawton | 528/289 |
| 4,141,928 | 2/1979 | Lawton | 260/860 |
| 4,148,764 | 4/1979 | Lamont | 260/22 D |
| 4,160,791 | 7/1979 | Higley et al. | 525/469 |
| 4,178,329 | 12/1979 | Becker et al. | 525/77 |
| 4,180,612 | 12/1979 | Paüze et al. | 528/289 |
| 4,181,606 | 1/1980 | Carden et al. | 210/22 A |
| 4,262,114 | 4/1981 | Wagener et al. | 528/301 |
| 4,293,669 | 10/1981 | Rottmaier et al. | 525/437 X |

FOREIGN PATENT DOCUMENTS

| | | |
|---|---|---|
| 2326963 | 1/1974 | Fed. Rep. of Germany . |
| 2541527 | 3/1976 | Fed. Rep. of Germany . |
| 53-10586 | 1/1978 | Japan . |

OTHER PUBLICATIONS

Nyilas et al, "Development of Blood-Compatible Elastomers, III, Hematologic Effects of Avcothane Intra-Aortic Balloon Pumps in Cardiac Patients", Journal of Biomedical Materials Research Symposium, No. 3, pp. 129-154 (1972).

Paik Sung et al, "Surface Chemical Analysis of Avcothane and Biomer by Fourier Transform IR Internal Reflection Spectroscopy", Journal of Biomedical Materials Research, vol. 12, pp. 791-804 (1978).

Ward et al, "Production of Biomedical Polymers I, Silicone/Urethane Synergy in Avcothane® Elastomers", Organometallic Polymers, Academic Press, Inc., pp. 219-229 (1078).

Gott, "Wall-Bonded Heparin—Historical Background and Current Clinical Applications", Heparin—Structure Function and Clinical Implications, pp. 351-363.

Nyilas, "Development of Blood Elastomers: Theory, Practice and in Vivo Performance", Delivered at 23rd ACEMB, Washington, D.C., Dec. 15-19, 1970.

Nyilas, "Development of Blood Compatible Elastomers II, Performance of Avocothane Blood Contact Surfaces in Experimental Animal Implantations", Journal of Biomedical Materials Research Symposium, No. 3, pp. 97-127 (1972).

Sa de Costa et al, Journal of Colloid and Interface Science, vol. 76, No. 2, Aug. 1980, pp. 594-596.

Halparin et al, "Heparin Covalently Bonded to Polymer Surface", Interaction of Liquid and Solid Substrates, Plenum Press, Oct. 28, 1968, pp. 197-205.

Falb et al, "Surface Bonded Heparin", Haparin—Structure Function and Clinical Implications, pp. 365-374.

Jones and Annis, "A Healing Bond Between Tissues and a Smooth Synthetic Polymer", Abstract of Talk Presented to Surgical Research Society, Jan. 5-6, 1973.

Lyman et al, "New Synthetic Membranes for Dialysis", Biochemistry, vol. 3, No. 7, Jul. 1964, pp. 985-990.

Gilding and Reid, "Biogradeable Polymers for Use in Surgery, Polyethylene Oxide, Polyethylene Terephthalate PEP/PET Copolymers", I (Untitled) and II, In Vitro Degradation, Polymer, vol. 20, Dec. 1979 at 1454 et seq. (5 pages) & vol. 22, Apr. 1981, pp. 499-504.

*Primary Examiner*—Lucille M. Phynes
*Attorney, Agent, or Firm*—Francis W. Young; Jack H. Hall

[57] ABSTRACT

Segmented copolyesters/copolyethers in which the soft segment polyethers incorporate a thermally stable heterocyclic unit, e.g., hydantoin, are found to be useful as biomedical materials since the heterocyclic ring prevents crystallization of the soft segment, and further provides a chemically reactive site for incorporating other moieties to enhance certain properties, e.g., heparin for increasing the non-thrombogenicity of the biocompatible material.

12 Claims, No Drawings

BIOCOMPATIBLE COPOLYMERS

FIELD OF THE INVENTION

This invention relates to the novel use of certain thermoplastic segmented copolyesters which are compatible with biological materials and possess significant properties which make them excellent biomedical materials.

BACKGROUND OF THE INVENTION

In recent years, a number of polymers have been developed, which are biocompatible, that is, do not cause tissue irritation or necrosis, platelet adhesion, or erythrocyte lysis.

One of the existing materials, polyvinyl chloride (PVC), has been widely used in blood tubing and blood bags; however, PVC is a rigid thrombogenic material which requires a plasticizer which may cause problems; e.g., some are suspected of being carcinogenic and others may alter the composition of the blood.

Biocompatible materials for contact with blood or tissue also have been made from block copolymers comprising alternate "hard" and "soft" segments. The hard segments confer the requisite physical properties, while the soft segments confer the desired biological properties upon the biocompatible materials. Since these segmented copolymers exhibit elasticity, the need for plasticizers, such as found in single component polymers, is avoided.

For example, commercial materials have become available in which the biocompatible material is a segmented polyether polyurethane [BIOMER® from Ethicon] and polydialkylsiloxane polyurethanes [AVCOTHANE® from Avco Medical Products]. Furthermore, polyester/polyether block copolymers having blood compatibility and therefore useful for shaping into biologically useful products have been described in Jones et al. U.S. Pat. Nos. 3,908,201 and 4,042,978 and Toyobo Japanese Pat. No. 53-10586.

While the segmented copolymers described above constituted a major advance in the state of the art, they, too, are deficient in some properties. For example, it is difficult to extrude the segmented urethanes into shapes from a melt.

Polyethylene oxide is widely employed as the polyether in both types of segmented copolymers, but when present in useful amounts, it is a crystalline material, having an attraction for blood platelets. It would appear from data reported by Decosta et al., JOURNAL OF COLLOID AND INTERFACE SCIENCE, VOL. 72, August 1980, pp. 594-596, that under the conditions under which their data was obtained, the polyethylene oxide segment (PEO) in the segmented polyurethanes is amorphous at low molecular weights; however, high molecular weight PEO is crystalline at greater than about ten percent (10%) concentration.

To use pure PEO, even at low concentrations, in blood contact applications, requires that the PEO must have a molecular weight of less than 2,000; otherwise, the soft segment will become crystalline. This limitation directly affects the physical properties of the polymer, because, for a given composition, the longer the chain length of the soft segment, the longer the length of the hard segment will be. Increasing the length of the hard segment enhances physical cross linking in these materials, especially in polyester based elastomers, which physical cross linking directly contributes to the strength and dimensional stability of these polymers.

The statement made above that the longer the soft segment, the longer the hard segment will be, can be demonstrated by reference to a given segmented copolyester composition having a fixed ratio of hard to soft segments (such as one which is 40% by weight polyester and 60% by weight polyester). Since (for a given composition) the mole fraction of a soft segment decreases by increasing its molecular weight, the use of higher molecular weight soft segments results in longer hard segments.

OBJECTS OF THE INVENTION

Accordingly, the object of the invention is to make a material which has adequate tensile properties, flexibility, tissue compatibility, non-thrombogenicity, non-adhesion of platelets, and which can be easily formed into any desired shapes by extrusion, molding or casting from solution.

It is a further object to make a material from which articles for storing or collecting blood can be made, which is permanently amorphous at temperatures at which blood is normally collected and stored.

It is also an object of the invention to provide a biocompatible material, and especially a blood compatible material, made from a copolymer having chemically reactive sites suitable for attachment of groups having significant biological function, e.g., heparin, to further prevent blood clotting, etc.

DESCRIPTION OF THE INVENTION

All of the objects of the invention set forth above are realized in accordance with the invention when biomedical devices and articles are made from a thermoplastic segmented copolyester having long-chain ester units and short-chain ester units joined through ester linkages wherein the long-chain ester units are polyethers incorporating at least one thermally stable heterocyclic ring, or "foreign" repeat unit, per molecule. The useful copolyesters are described in U.S. Pat. No. 4,262,114, which is hereby incorporated in its entirety by reference.

In particular, Applicant has found, unexpectedly, that the copolyester polyethers disclosed in the aforesaid patent contain sufficient long-chain ester units incorporating the foreign repeat unit that crystallization of the soft segment is prevented at the temperature and under conditions at which the biocompatible material is normally used.

The presence of the "foreign" unit in the polyoxyethylene prepolymer reduces the polymer's propensity to crystallize, simply because it is a foreign unit in the polymer chain. Since the chemistry used to prepare the polyoxyethylene polymer essentially places the "foreign" unit in the center of the polyether chain, it effectively divides the crystallizeable molecular weight of the polyether in half. This means that the total molecular weight of the polyether can be doubled (to at least 4,000) prior to the onset of crystallization difficulties in the polyether. This "doubling" of the useful molecular weight in the polyether translates into better physical properties in the copolymer, especially in compositions containing relatively higher weight percentages of polyether.

In particular, the advantages of the invention are realized by forming biomedical articles from a segmented thermoplastic copolyester consisting essentially of a multiplicity of recurring long-chain ester units and short-chain ester units joined head to tail through ester linkages, said long-chain ester units comprising from 30–70% by weight of the copolyester and being represented by the formula:

(I)

and said short-chain ester units being represented by the formula:

(II)

where L in said long-chain unit is a divalent radical remaining after removal of terminal hydroxyl groups from a poly(oxyalkylene) glycol having at least one thermally stable heterocyclic ring per molecule, each of said rings attached to said chain through amide or amide linkages and giving said radical, L, a carbon to nitrogen ratio between about 3/1 and about 350/1, and a number average molecular weight of between 200 and 8,000 and preferably from 800 to 4,000; R is a divalent radical remaining after removal of carboxyl groups from a dicarboxylic acid having a molecular weight of less than 300; and E in said short-chain unit is a divalent radical remaining after removal of hydroxyl groups from a low molecular weight diol having 2 to 15 carbon atoms per molecule and a molecular weight less than about 250.

Heterocyclic, nitrogen-containing rings, which may comprise the "foreign repeat unit" described in the aforesaid U.S. Pat. No. 4,262,114 and can covalently link along the soft segment chain as amide or imide, include: 1,3-divalent-5,5-dialkylhydantoin (including alkyl groups connected in a cyclic fashion to the 5,5 positions); 1,3-divalent-5-alkyl-5-phenyl hydantoin and 1,3-divalent-5,5-diphenyl hydantoin (including substituted phenyl); 2,5-divalent-1,3,4-triazole; 2,5-divalent-1,3,4-oxadiazole; 2,-5-divalent-1,3,4-thiadiazole; 1,3-divalent-1,2,4-triazolidine-3,5-dione; 4,5-divalent-1,2-isothiazole; 4,5-divalent-1,2-oxazole; 4,5-divalent-1,3-diazole; 2,5-divalent-1,3-oxazole; 2,4-divalent-imidazole; divalent (N position) hypoxanthine; and 2,5-divalent-1,3-thiazole, and the acyl chlorides or isocyanate derivative thereof.

One preferred heterocyclic ring unit is 1,3-divalent 5,5-dimethyl hydantoin; another preferred heterocyclic ring unit is a hydantoin unit having a chemically reactive site, for example, the 5-acyl chloride of a 1,3-divalent-5-alkyl hydantoin having the following structure:

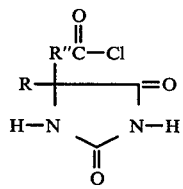

These copolymers may contain a wide range of hydantoin polyether (HPOE) weight percentages, from as low as 1% to as high as 95%. As the percentage of HPOE increases, blood compatibility increases and the strength of the segmented copolymer decreases. A useful range of HPOE varies from 20% to 80%, depending upon the application. For example, segmented copolymers of this type might be used for blood lines, blood bags, and other devices requiring strength and blood- and biocompatibility during relatively short exposure times. HPOE percentages can vary from 30% to 60% for these applications. Where strength is not an important feature, however, the percentage of HPOE can be further increased to as high as 80%; for example, in HPOE-containing copolymers coated onto the surface of other materials to improve their blood and biocompatibility.

It is believed that the more soft segment of the copolymers that is located at the surface of the polymer molecule, the greater will be the blood compatibility of the copolymer. It is also theorized that the greater the phase separation of the two segments, the more soft segment will be found at the surface. Therefore, it it suggested that to increase blood compatibility of the copolymer, one should control the phase separation so as to obtain the greatest degree of phase separation possible. Electron Spectroscopy Chemical Analysis (ESCA) examination of applicants' copolymer indicated that the surface is comprised of virtually all soft segment indicating excellent phase separation in the preparation of the polymer.

Several ways of increasing phase separation are possible, for example, by slower cooling of the melt, by casting from a solution rather than a melt, by choosing a solvent which is a better solvent for the soft segment than for the hard segment, etc.

As stated earlier, the soft segment (HPOE) of this copolymer has a site, namely, the hydantoin ring, which allows the attachment of virtually any chemical moiety to this portion of the copolymer. Since the soft segment is the portion of the polymer which is actually found at the surface, and, therefore, in direct contact with blood and tissue, the attached chemical moiety can perform a number of functions which might be advantageous, one of which would be to further enhance the compatibility of the surface with its environment. For example, when the copolymer is in contact with blood, it might be useful to attach heparin, a well known anticoagulant, thus increasing the blandness of the polymer's surface.

The attachment of a new chemical moiety to HPOE occurs by selecting the proper reagents for the Bucherer synthesis, which is the most convenient general method for preparing 5,5-disubstituted hydantoin rings. An aldehyde (or ketone) in aqueous alcohol is heated at 60%–70% with potassium cyanide and ammonium carbonate. Ammonium carbonate, $(NH_4)_2CO_3$, can be generated in situ, if desired, with $CO_2$, $NH_3$ and $H_2O$. Reaction times are short and yields are generally high. The chemistry is found below. The functionality for attachment of heparin may be an acid chloride having 3–15 carbon atoms in the acyl group (to form an ester) or an isocyanate having 3–15 carbon atoms (to form a urethane). Thus, the new chemical moiety desired in the soft segment is derived from the proper selection of an aldehyde or ketone, e.g.:

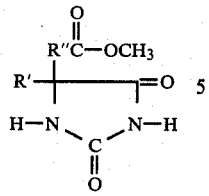

where
R′=C₁-C₃ lower alkyl or R″ and
R″=divalent C₃-C₁₅ alkyl or phenyl

Once the chemical moiety has been incorporated in the hydantoin ring, the nitrogens are then ethoxylated to yield substituted HPOE.

Note that the desired chemical moiety could be attached either before or after ethoxylation is done. Also, it should be noted that the chemical moiety could be attached to the soft segment after the soft segment has been incorporated in the copolymer. Heparin has the proposed structure:

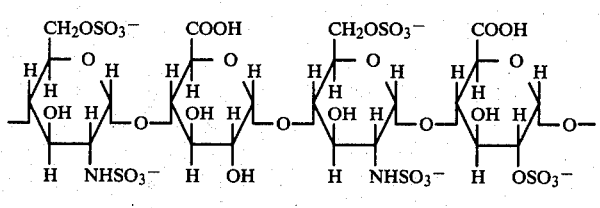

which exhibits three functional groups capable of reacting with linking groups that would attach it to HPOE. However, one must choose a group which is not involved in heparin's biological activity. Most researchers choose the hydroxy function as a position of attachment. Further representation of heparin will be Hep—OH, then, to simplify schematics.

Most commonly, Hep—OH is attached via acylation or urethane formation, and of the two methods, acylation is preferred from a blood compatibility point of view, since the hydrogen bond present in the urethane link is thought to induce thrombogenicity. Thus, Hep—OH should be linked to HPOE via acylation to form an ester group.

The length of R‴ plays an important role, since it has been reported that if heparin is too closely bound to a surface, its activity is lost. The preferred substituents are R‴=C₉₋₁₅. Instead of chlorides, other halides may be used.

The following synthetic scheme is illustrative of how such a heparin-bonded structure can be formed.

REACTION 1

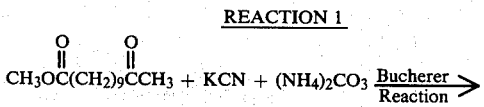

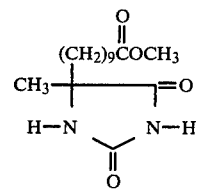

REACTION 2

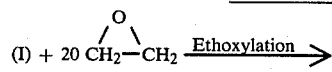

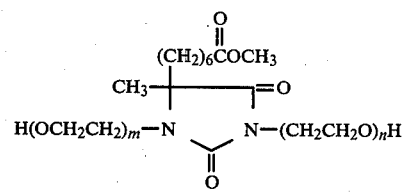

REACTION 3

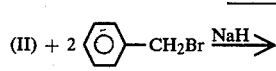

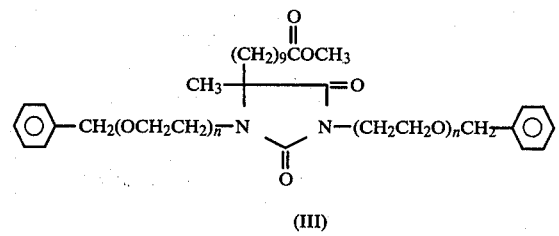

REACTION 4

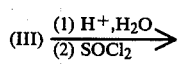

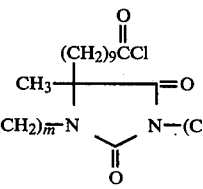

REACTION 5

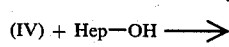

-continued

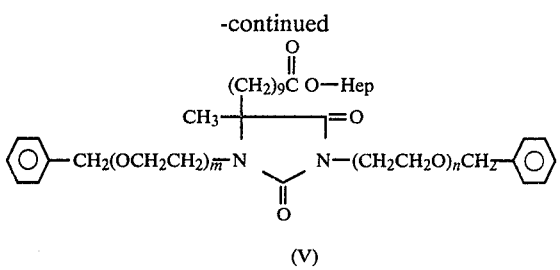

(V)

REACTION 6

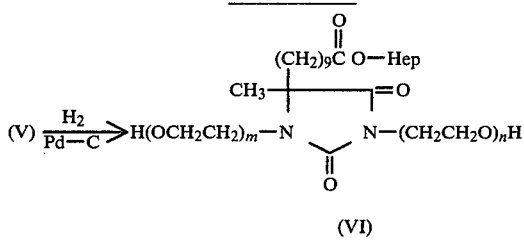

(VI)

REACTION 7

(VI) + HO(CH₂)₄OH +

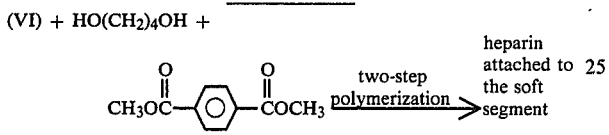

In reaction 1, a Bucherer synthesis is performed using a ketone containing a methyl ester group, the ultimate site of the acid chloride group. This group is masked as a methyl ester to allow for smooth ethoxylation of the hydantoin nitrogens (Reaction 2). Once ethoxylation is complete, the alcohol functions are masked (Reaction 3) to prevent their interference with acid chloride formation (Reaction 4). In reaction 5, heparin is attached to the reactive site of the hydantoin group. In Reaction 6, the hydroxy groups are freed for copolymer formation (Reaction 7).

Of course, other schemes exist to attach heparin to the already formed copolymer.

The hard segment may be polyethylene terephthalate, 1,4-cyclohexanedimethylol terephthalate, polybutylene terephthalate, etc. The preferred hard segment or long-chain ester unit is polybutylene terephthalate (PBT). The weight percentages of the soft segment and hard segment may be varied during synthesis so as to obtain a family of polymers whose properties vary with the composition. It has been found that increasing the weight percentage of the soft segment results in an increase in elongation, elastic recovery, stress decay, and flexibility, with a concomitant loss in strength, chemical stability, melting point and ease of extrusion. Furthermore, blood compatibility and bio-compatibility in general should increase with increasing weight percentage of the soft segment, assuming that the negative effects of leachable, low molecular weight products can be eliminated. It is believed that the unexpectedly high degree of compatibility with biological materials is due primarily to the incorporation of heterocyclic, e.g., hydantoin, units into the long-chain ester unit or soft segment, and is due to the amorphous nature or lack of crystallinity in the soft segment. It is believed that the introduction of the "foreign unit" interrupts the regularity of the polyether segment, and supresses its melting point to thereby prevent crystallization at room temperature.

EXAMPLE 1

A copolymer [A] was prepared as in Example 3 of U.S. Pat. No. 4,262,114, having a 50% by weight hard segment, comprising polybutylene terephthalate and 50% by weight soft segment, comprising hydantoin polyoxyethylene, using a hydantoin-containing segment of prepolymer prepared as in Example 1 of said patent, having a molecular weight of 1,200. Additional samples were prepared in the same manner, except that ratios of PBT to HPOE were 70:30 [B], 30:70 [C], 60:40 [D], and 45:55 [E].

The blood compatibility of the 30:70 polymer [C] was tested according to the procedure described in the article In Vitro Assessment of Interaction of Blood With Model Surfaces by Lindon et al. JOURNAL OF LABORATORY AND CLINICAL MEDICINE, VOL. 92, pp. 904–915 (December 1978). This material had a platelet recovery index (PRI) of 0.90. A control sample consisting of 30% polyester/70% polyethylene oxide (1000 molecular weight) under conditions in which the polyethylene oxide segment was amorphous, gave a PRI of about 0.94. Statistically, however, there is no difference between the respective PRI results.

Portions of extruded film from each of the samples having ratios of 60:40 [D] and 45:55 [E], respectively, were cut to form bags by heat sealing along two edges, leaving the tops open. Into one bag of each sample, 1.5 ml of heparinized rabbit blood was introduced. The bags were transferred to a refrigerator and observed over a 72-hour period. The sedimentation rate was normal for each film sample. No hemolysis was seen at 72 hours; the plasma portion was perfectly clear. Neither sample interfered with the anticoagulant action of the heparin.

One and one-half ml of whole rabbit blood, unheparinized, was placed into another bag of each of the [D] and [E] samples. The samples clotted within six (6) minutes with no hemolysis, i.e., within the normal clotting time range.

In a second test, small strips of each of the 60:40 and 45:55 copolymers were placed in small beakers. The strips were then covered with 5 ml of heparinized whole rabbit blood. The beakers were transferred to a refrigerator overnight. Upon settling of the cells, the plasma in the beakers was clear, straw-colored, with no hemolysis.

Neither film causes hemolysis on standing up to 72 hours, and neither film sample interferes with the anticoagulant action of heparin.

Several of the samples were further tested for toxicity of the polymeric materials on biomaterials. In the Tissue Culture-Agar Overlay Test (Guess, W. L. et al., "Agar Diffusion Method for Toxicity Screening of Plastics on Cultured Cell Monolayers, " J. Pharm. Sci., 54, 156 (1965) as modified in "Primary Acute Toxicity Screening Protocols For Biomaterials" procedure published by the Materials Science Toxicology Laboratories of The University of Tennessee, Center for the Health Science, Memphis, Tenn. 38163, the 70:30 PBT/HPOE [B] and 50:50 PBT/HPOE [A] were found to be a non-cytotoxic, while the 30:70 PBT/HPOE [C] was recorded as cytotoxic. However, it is believed that the latter material can be rendered non-cytotoxic by removing low molecular weight polyether compounds; for example, by dissolving and reprecipitating or perhaps merely by washing or through postcondensation of the low molecular weight compounds.

In a further test of hemolysis action of the polymers using rabbit blood, the 70:30 [B] and 50:50 [A] samples referred to showed 1% and 0% hemolysis, respectively (values of 5% of less are considered as non-hemolytic). Sample C (30/70 PBT/HPOE) exhibited 60% hemolysis.

Each of the three samples, A, B, and C, was extracted at 120° in an autoclave for one hour with each of the following extracting media: saline; polyethylene glycol 400 and cottonseed oil. These extracts were then included in the Tissue Culture-Agar Overlay test to determine toxicity of the extracts and also for cell growth inhibition according to the Inhibition of Cell Growth Assay (Leachability-Toxicity profile) from the "Primary Acute Toxicity Screening Protocols for Biomaterials" ATTP-I, p. 52–59 as amended, available from the Materials Science Toxicology Laboratories of The University of Tennessee Center for the Health Sciences, Memphis, Tenn. 38163. The results of the Tissue Culture-Agar Overlay test are as follows:

| TISSUE CULTURE AGAR OVERLAY TEST | | |
|---|---|---|
| PBT/HPOE | | |
| 50:50 [A] | Saline | Noncytotoxic (1/0) |
| | Polyethylene Glycol 400 | Noncytotoxic (1/0) |
| | Cottonseed Oil | Cytotoxic (1/1) |
| 70:30 [B] | Saline | Noncytotoxic (1/0) |
| | Polyethylene Glycol 400 | Noncytotoxic (1/0) |
| | Cottonseed Oil | Cytotoxic (1/1) |
| 30:70 [C] | Saline | Cytotoxic (1/1) |
| | Polyethylene Glycol 400 | Cytotoxic (1/1) |
| | Cottonseed Oil | Cytotoxic (1/2) |
| Negative Control | | Noncytotoxic (0/0) |
| Positive Control | | Cytotoxic (3/4) |

Note:
Values of (0/0) and/or (1/0) are recorded as noncytotoxic; values above these are cytotoxic. (The first number, on a scale of 1 to 5, indicates the degree of discoloration in a dyed area around the sample. The second number is the extent of cell lysis.)

In the Cell Growth Inhibition Assay, the 70:30 PBT/HPOE sample did not produce a significant increase in cell growth inhibition at any of the sample weights. The 50:50 PBT/HPOE sample did not produce any significant increase in cell growth inhibition with sample weights up to 400 mg, although a significant increase in cell growth inhibition (100%) was produced with a sample weight of 4000 mg. The 30:70 PBT/HPOE sample did not produce any significant increase in cell growth inhibition with sample weights up to 100 mg, although a significant increase was noted with sample weights of 500 mg (96% increase) and 4000 mg (100% increase).

EXAMPLE 2

Synthesis of the heparin containing poly(ester ether) may be accomplished in 7 steps, described in the specification and exemplified below.

Methyl-(11-keto-laurate), 0.44 mol, is dissolved in 1 liter of aqueous ethanol followed by the addition of 0.7 mol each of potassium cyanide and ammonium carbonate. The reaction volume is heated at 60°–70° C. for 24 hours, yielding the keto substituted hydantoin, (I), in 50% yield. The product is purified by crystallization from ethanol-water.

The substituted hydantoin, I, is converted to a polyether in two steps. First, two moles of ethylene oxide (EO) are added in a pressure vessel under normal ethoxylation conditions, and this 2 mol EO-adduct is crystallized from ethanol/water. This product is then further ethoxylated under normal pressure conditions until a total of 20 mols of ethylene oxide have been added to each mole of (I), yielding structure (II).

The hydroxyl end groups of structure (II) must be protected with benzyl ether groups to prevent their interference in subsequent reactions. Structure (II) in tetrahydrofuran (THF) is treated with a 1 molar excess of sodium hydride thus converting it to the dialkoxide salt. A one molar excess of benzyl bromide (3 mols benzyl bromide per mole of di-alkoxide salt) is added to the reaction, and the mixture is refluxed for 5 hours. Sodium bromide is filtered and the diether is purified via liquid chromatography using THF as the primary solvent to yield structure (III) in 40% yield.

Under the procedure described below, the protected polyether (structure III) then is hydrolyzed under mild acid conditions, followed by acid chloride formation. Aqueous THF acidified with HCl is refluxed with 0.1 mol (140 grams) of structure (III), followed by the addition of 0.2 mols of thionyl chloride. The solution is refluxed for 6 hours, and the product is again purified via liquid chromatography. Yields of structure (IV) are 25%.

Heparin is then attached to the hydantoin ring via ester formation with a heparin alcohol group and the acid chloride function using dimethylacetamide (DMAc) as the solvent. One hundred grams of structure (IV) are dissolved in DMAc and 500 mg of heparin are added. The mixture is stirred at room temperature under nitrogen and the product, structure (V), is filtered and washed with water. The benzyl groups are then removed by treatment with hydrogen and a Pd-C catalyst, yielding structure (VI), the desired monomer for polymerization.

Polymerization can be done using dimethyl terephthalate (DMT), 1,4-butanediol and structure (VI). 1.2 mols of 1,4-butanediol and 1.0 mol of DMT are reacted in the bulk at 185° C. to 220° C., using tetramethyltitanate as a catalyst (600 ppm Ti on DMT). Once this transesterification is complete, 100 grams of structure VI is added, and the polymerization is completed under vacuum (0.1 mm Hg) at 250° C., giving an off-white product having a relative viscosity of 3.10 (1% polymer in 60/40 phenol/tetrachloroethane).

I claim:

1. A process for making articles which are compatible with biological materials, the improvement comprising forming said articles from a segmented thermoplastic copolyester consisting essentially of a multiplicity of recurring long-chain ester units and short-chain ester units joined head to tail through ester linkages, said long-chain ester units comprising from 30–70% by weight of the copolyester and being represented by the formula:

and said short-chain ester units being represented by the formula:

where L in said long-chain unit is a divalent radical remaining after removal of terminal hydroxyl groups from a poly(oxyalkylene) glycol having at least one thermally stable heterocyclic ring per molecule, each of said rings attached to said chain through amide or imide linkages and giving said radical, L, a carbon to nitrogen ratio between about 3/1 and about 350/1, and a number average molecular weight of between 200 and 8,000; R is a divalent radical remaining after removal of carboxyl groups from a dicarboxylic acid having a molecular weight of less than 300; and E in said short-chain unit is a divalent radical remaining after removal of hydroxyl groups from a low molecular weight diol having 2 to 15 carbon atoms per molecule and a molecular weight less than about 250.

2. The process of claim 1, wherein said heterocyclic ring is derived from a divalent hydantoin-containing monomer.

3. The process of claim 2, wherein said hydantoin-containing monomer has a chemically reactive site.

4. The process of claims 1, 2 or 3, wherein substantially all of the dicarboxylic acid is terephthalic acid.

5. The process of claims 1, 2 or 3, wherein substantially all the low molecular weight diol is 1,4-butane diol.

6. The process of claims 1, 2 or 3, wherein the poly(oxyalkylene) glycol is poly(oxethylene) glycol having a molecular weight of about 800–4000.

7. The process of claim 2, wherein said hydantoin-containing monomer has the structure:

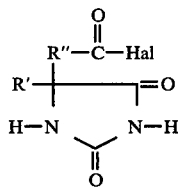

wherein
R'=alkyl having 1–3 carbons,
Hal=F, Cl, Br, I and
R"=alkyl having 3–15 carbons.

8. The process of claims 3 or 7, wherein at least one heparin moiety is chemically attached to said reactive site.

9. A biocompatible article, adaptable for biomedical uses, said article being made from a segmented, thermoplastic copolyester consisting essentially of a multiplicity of recurring non-crystalline long-chain ester units and short-chain ester units joined head to tail through ester linkages, said long-chain ester units comprising from 30–70% by weight of the copolyester and being represented by the formula:

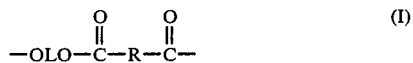

and said short-chain ester units being represented by the formula

where L in said long-chain unit is a divalent radical remaining after removal of terminal hydroxyl groups from a poly(oxyalkylene) glycol having at least one thermally stable heterocyclic ring per molecule, each of said rings attached to said chain through amide or imide linkages and giving said radical, L, a carbon to nitrogen ratio between about 3/1 and about 350/1, and a number average molecular weight of between 200 and 8,000; R is a divalent radical remaining after removal of carboxyl groups from dicarboxylic acid having a molecular weight of less than 300; and E in said short-chain unit is a divalent radical remaining after removal of hydroxyl groups from a low molecular weight diol having 2 to 15 carbon atoms per molecule and a molecular weight less than about 250.

10. The article of claim 9, wherein said heterocyclic ring is derived from a divalent hydantoin-containing monomer having a chemically reactive site.

11. The article of claim 10, wherein said hydantoin-containing monomer has the structure:

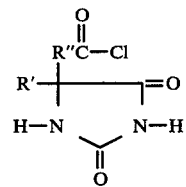

wherein
R'=alkyl having 1–3 carbons and
R"=alkyl having 3–15 carbons.

12. The article of claim 11, wherein at least one heparin moiety is chemically attached to each of said reactive sites.

* * * * *